(12) United States Patent
Szczepanski et al.

(10) Patent No.: US 10,184,876 B2
(45) Date of Patent: Jan. 22, 2019

(54) PARTICULATE MATTER SENSOR

(71) Applicant: DENSO International America, Inc., Southfield, MI (US)

(72) Inventors: Edward Szczepanski, Grosse Pointe Woods, MI (US); Richard Hankins, Brighton, MI (US); Rafal Kaput, Sterling Heights, MI (US); Michael Lewis, Dearborn, MI (US); Masayuki Kobayashi, Farmington Hills, MI (US)

(73) Assignee: DENSO International America, Inc., Southfield, MI (US)

( * ) Notice: Subject to any disclaimer, the term of this patent is extended or adjusted under 35 U.S.C. 154(b) by 114 days.

(21) Appl. No.: 15/263,894

(22) Filed: Sep. 13, 2016

(65) Prior Publication Data

US 2018/0073971 A1    Mar. 15, 2018

(51) Int. Cl.
| | |
|---|---|
| *G01N 15/06* | (2006.01) |
| *F01N 11/00* | (2006.01) |
| *G01N 29/02* | (2006.01) |
| *F01N 13/18* | (2010.01) |
| *G01N 29/036* | (2006.01) |
| *G01N 29/24* | (2006.01) |
| *G01N 29/44* | (2006.01) |
| *G01N 15/00* | (2006.01) |

(52) U.S. Cl.
CPC ......... *G01N 15/0656* (2013.01); *F01N 11/00* (2013.01); *F01N 13/18* (2013.01); *G01N 15/0606* (2013.01); *G01N 29/02* (2013.01); *G01N 29/036* (2013.01); *G01N 29/2437* (2013.01); *G01N 29/4427* (2013.01); *F01N 2550/04* (2013.01); *F01N 2560/05* (2013.01); *F01N 2560/20* (2013.01); *G01N 2015/0046* (2013.01); *G01N 2291/014* (2013.01); *G01N 2291/021* (2013.01); *G01N 2291/0217* (2013.01)

(58) Field of Classification Search
CPC ........................... G01N 15/0656; G01N 29/02
USPC ........................................................ 73/23.31
See application file for complete search history.

(56) References Cited

U.S. PATENT DOCUMENTS

| | | | |
|---|---|---|---|
| 4,254,354 A * | 3/1981 | Keem ................. | G01P 15/0922 310/321 |
| 7,194,891 B2 | 3/2007 | Tuller et al. | |
| 2008/0202108 A1* | 8/2008 | Stritzinger ............ | F01N 3/2066 60/301 |
| 2010/0126248 A1* | 5/2010 | Hall ...................... | G01N 27/22 73/23.33 |
| 2012/0151992 A1 | 6/2012 | Harada et al. | |
| 2014/0305191 A1* | 10/2014 | Schmid ................ | G01N 29/022 73/24.03 |

* cited by examiner

*Primary Examiner* — Son T Le
*Assistant Examiner* — Tarun Sinha
(74) *Attorney, Agent, or Firm* — Harness, Dickey & Pierce, P.L.C.

(57) ABSTRACT

A particulate matter sensor assembly including a resistance sensor and a resonance sensor. Each one of the resistance sensor and the resonance sensor is configured to measure particulate matter present in engine exhaust.

15 Claims, 2 Drawing Sheets

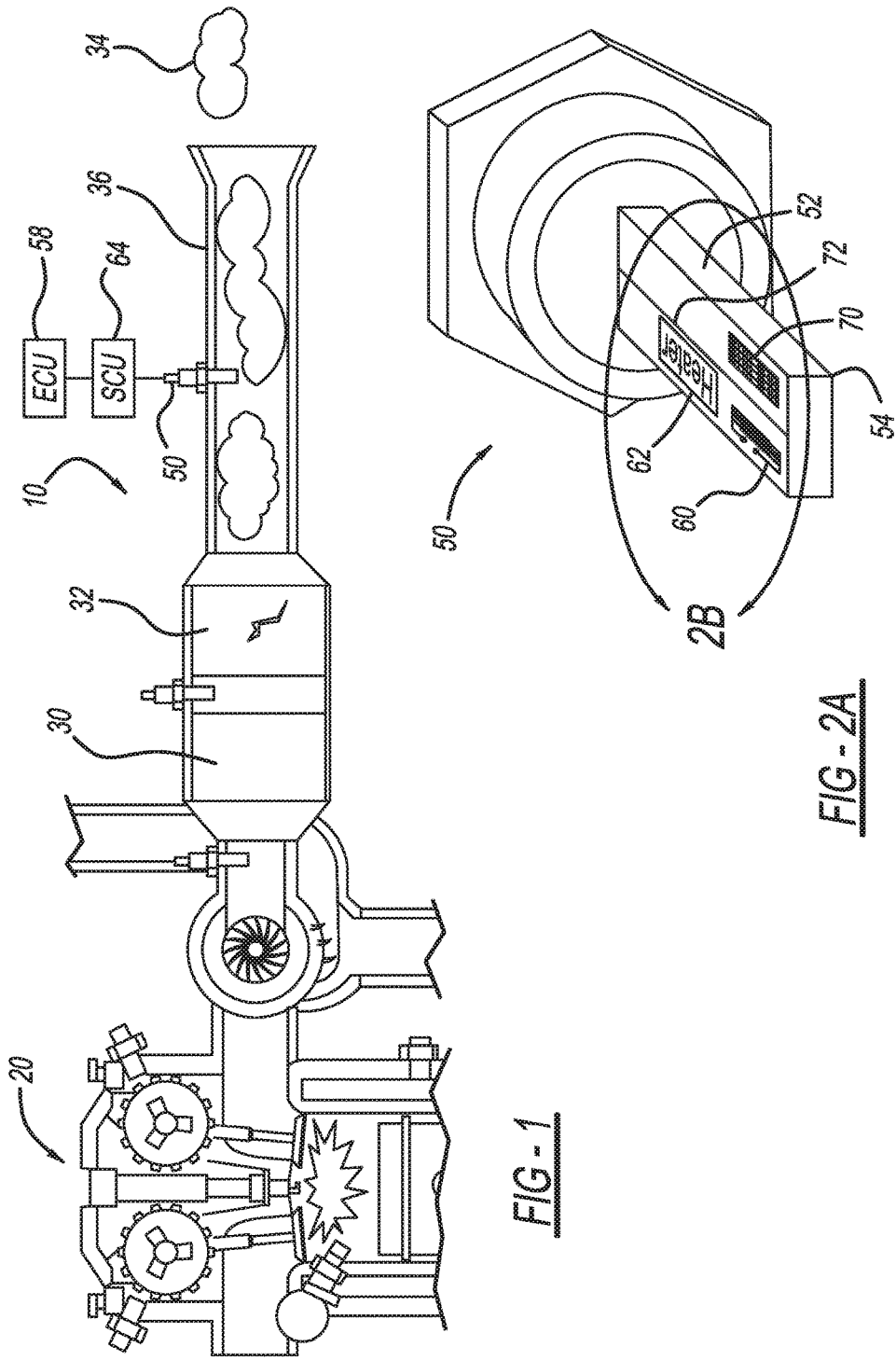

PARTICULATE MATTER SENSOR

FIELD

The present disclosure relates to a particulate matter sensor, such as a particulate matter sensor for engine exhaust.

BACKGROUND

This section provides background information related to the present disclosure, which is not necessarily prior art.

Exhaust treatment systems treat engine exhaust before the exhaust is released into the atmosphere, such as by filtering undesirable particles from the exhaust. For example, exhaust treatment systems often include a particulate filter that filters soot and other particulates from the exhaust. To determine whether the particulate filter is operating properly, a particulate matter sensor is arranged downstream of the particulate filter to measure the particulate content of the exhaust.

Some particulate matter sensors include a resistance sensor, which changes resistance in response to a buildup of particulates thereon that should have been filtered by the particulate filter. If the sensor measures an unacceptable level of particulates in the exhaust, it is likely that the particulate filter is not operating properly. For example, the particulate filter may be cracked, thereby reducing its effectiveness. While current particulate matter sensors are suitable for their intended use, they are subject to improvement. For example, the resistance sensor may fail or become inaccurate, thereby making it difficult to determine whether the particulate filter is operating properly. The present teachings provide for an improved particulate matter sensor that addresses this issue, as well as numerous others.

SUMMARY

This section provides a general summary of the disclosure, and is not a comprehensive disclosure of its full scope or all of its features.

The present teachings provide for a particulate matter sensor assembly including a resistance sensor and a resonance sensor. Each one of the resistance sensor and the resonance sensor is configured to measure particulate matter present in engine exhaust.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of select embodiments and not all possible implementations, and are not intended to limit the scope of the present disclosure.

FIG. 1 illustrates an engine, an exhaust treatment system for treating exhaust from the engine, and a particulate matter sensor according to the present teachings;

FIG. 2A is a perspective view of a probe tip of the particulate matter sensor;

Corresponding reference numerals indicate corresponding parts throughout the several views of the drawings.

DETAILED DESCRIPTION

Figure 2B:
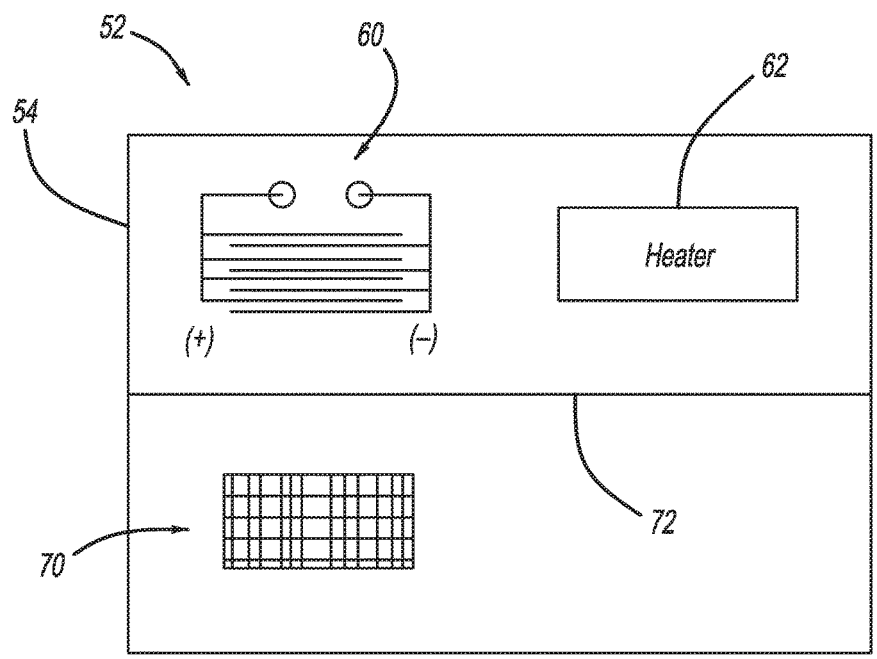
FIG. 2B is a plan view of area 2B of FIG. 2A.

Example embodiments will now be described more fully with reference to the accompanying drawings.

With initial reference to FIG. 1, an exhaust treatment system 10 for treating exhaust from an engine 20 is illustrated. The engine 20 may be any engine that releases exhaust including particulate matter to be filtered prior to being released to the atmosphere. For example, the engine 20 can be an automobile engine, an engine for a mass transit vehicle, a military vehicle engine, a watercraft engine, a generator engine, an aircraft engine, etc.

To treat exhaust released from the engine 20, the exhaust treatment system 10 includes a catalyst 30, such as a three-way catalyst, and a particulate filter 32. The catalyst 30 can be any suitable catalyst configured to convert gasses and pollutants in the exhaust to less toxic pollutants by catalyzing a redox reaction. The particulate filter 32 can be any suitable filter configured to filter particulate matter out of exhaust 34 prior to the exhaust 34 entering exhaust outlet (or tailpipe) 36 and being released to the atmosphere.

Downstream of the particulate filter 32 (with respect to the flow of exhaust 34 from the engine 20 to the atmosphere) is a particulate matter sensor assembly 50. In the example of FIG. 1, the particulate matter sensor assembly 50 is arranged along the exhaust outlet 36. The particulate matter sensor assembly 50 is configured to measure the amount of particulate matter present in the exhaust 34, such as the amount of soot and other particulates.

With continued reference to FIG. 1 and additional reference to FIGS. 2A and 2B, the particulate matter sensor 50 includes a probe tip 52 having a distal end 54. The sensor 50 is arranged at the exhaust outlet 36 such that the probe tip 52 and the distal end 54 extend into the exhaust outlet 36 so as to be in contact with the exhaust 34 flowing from the particulate filter 32 and through the exhaust outlet 36 to the atmosphere. The probe tip 52 includes a resistance sensor 60, which can be located at any suitable position about the probe tip 52 and can be any suitable resistor configured to change resistance in response to buildup of particulate matter thereon. Thus when resistance of the resistance sensor 60 increases above a predetermined threshold in response to buildup of particulate matter thereon, this indicates that the particulate filter 32 is not functioning optimally to filter particulate matter out of the exhaust 34 (the particulate filter 32 may be cracked, for example). The resistance sensor 60 can be in communication with any suitable controller, such as an engine control unit (ECU) 58 for the engine 20 and/or a sensor control unit (SCU) 64. The resistance sensor 60 can be in communication with the ECU 58 directly or by way of the SCU 64. When the ECU 58 or SCU 64 determines that the resistance of the resistance sensor 60 has exceeded a predetermined threshold, the ECU 58 or SCU 64 can generate an alert indicating that the particulate filter 32 should be checked, such as for cracks.

The probe tip 52 further includes a heater 62. The heater 62 can be at any suitable location about the probe tip 52 and can be any heater suitable to heat the resistance sensor 60 in order to regenerate the resistance sensor 60 in the event that an excessive amount of particulate matter builds up on the resistance sensor 60, thereby reducing the effectiveness of the resistance sensor 60. The heater 62 can be activated by the ECU 58 or SCU 64 when the ECU 58 or SCU 64 determines that an excessive amount of particulate matter has built up on the resistance sensor 60.

The probe tip 52 further includes a resonance sensor 70, which can be at any suitable position about the probe tip 52. The resonance sensor 70 can be any suitable resonance sensor, such as a piezoelectric sensor. The resonance sensor 70 uses the piezoelectric effect to measure changes in resonance of an acoustic wave generated by the sensor 70. Changes in resonance directly correspond to the amount of particulate matter in the exhaust 34. For example, an increase in resonance represents an increase of particulate matter present in the exhaust 34. An increase in resonance above a predetermined level indicates that the amount of particulate matter present in the exhaust 34 is greater than an acceptable level, and that the particulate filter 32 is not functioning properly (i.e., may be cracked). Thus both the resistance sensor 60 and the resonance sensor 70 are configured to measure the amount of particulate matter present in the exhaust 34, but do so in different ways.

The resonance sensor 70 can be configured as a backup to the resistance sensor 60. For example, the resonance sensor 70 can be used if the heater 62 fails, thus preventing the resistance sensor 60 from being regenerated (i.e., cleaned), which will prevent the resistance sensor 60 from accurately measuring the amount of particulate matter present in the exhaust 34. The resonance sensor 70 can be used by the ECU 58 or SCU 64 to measure particulate matter in the exhaust 34 in order to determine whether or not the particulate filter 32 is operating optimally. The resonance sensor 70 is cleaned or regenerated not by the heater 62, but by cycling through a number of vibration sweeps configured to clear particulate matter that has built up on the resonance sensor 70. Thus any failure of the heater 62 will not affect the resonance sensor 70.

The resonance sensor 70 need not be constantly in operation. It can merely be activated, such as by the ECU 58 or SCU 64, when the ECU 58 or SCU 64 determines that the resistance sensor 60 is not functioning optimally. The resonance sensor 70 can be configured to trigger an onboard diagnostic notification signal in the event that the resistance sensor 60 is not functioning optimally. Once the operation of the resistance sensor 60 is restored, the ECU 58 or SCU 64 can reestablish the resistance sensor 60 as the primary particulate matter sensor, and again rely on the resonance sensor 70 as a backup to the resistance sensor 60.

The resonance sensor 70 can also be used to calibrate the accuracy of the resistance sensor 60. For example, there may be a tolerance for how close together resistance beads of the resistance sensor 60 can be arranged. Thus if particulate matter smaller than designed parameters contacts the resistance sensor 60, presence of the particulate matter may not be detected by the resistance sensor 60. The resonance sensor 70, however, is configured to detect particulate matter of nearly any size, and thus the resonance sensor 70 can be used to calibrate against the accuracy of the resistance sensor 60.

Figure 3:
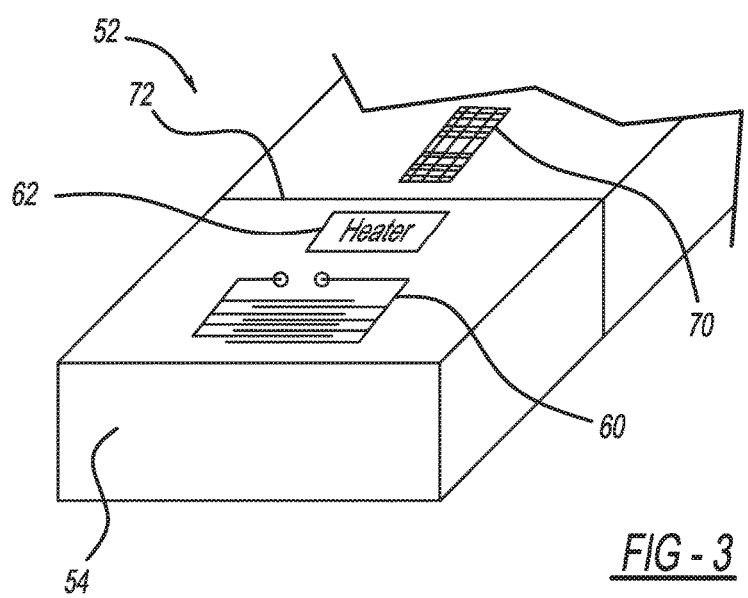
FIG. 3 is a perspective view of the distal end of the probe tip in accordance with another configuration according to the present teachings.

The probe tip 52 further includes an insulator 72, which is configured to insulate the resonance sensor 70 from the heater 62 and the resistance sensor 60. The insulator 72 can be any suitable insulator, such as a ceramic insulator, any other suitable heat shield, or recessed slot. The insulator 70 can be arranged at any suitable position on the probe tip 52. For example, the insulator 70 can extend along a length of the probe tip 52 as illustrated in FIG. 2A, or along a width of the probe tip 52 as illustrated in FIG. 3. With reference to FIG. 3, the resistance sensor 60 can be arranged proximate to the distal end 54, while the resonance sensor 70 can be arranged spaced apart from the distal end 54. To insulate the resonance sensor 70, the insulator 72 can be arranged between the resonance sensor 70 and both the resistance sensor 60 and the heater 62.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A particulate matter sensor assembly comprising:
   a resistance sensor;
   a resonance sensor; and
   a sensor probe having a probe tip, the probe tip includes:
      the resistance sensor, a heater proximate to the resistance sensor to heat the resistance sensor, the resonance sensor, and an insulator insulating the resonance sensor from the heater;
   wherein each one of the resistance sensor and the resonance sensor is configured to measure particulate matter present in engine exhaust.

2. The particulate matter sensor assembly of claim 1, wherein the resonance sensor is a piezoelectric sensor.

3. The particulate matter sensor assembly of claim 1, wherein the resonance sensor is an acoustic wave sensor.

4. The particulate matter sensor assembly of claim 1, wherein the insulator is a heat shield insulating the resonance sensor from the resistance sensor.

5. The particulate matter sensor assembly of claim 1, wherein the insulator is a ceramic insulator insulating the resonance sensor from the resistance sensor.

6. The particulate matter sensor assembly of claim 1, wherein the insulator is a slot between the resistance sensor and the resonance sensor configured to thermally insulate the resistance sensor from the resonance sensor.

7. The particulate matter sensor assembly of claim 1, wherein the heater is configured to heat the resistance sensor to regenerate the resistance sensor.

8. The particulate matter sensor assembly of claim 1, wherein the resonance sensor is a backup sensor configured to operate when the resistance sensor is not functioning.

9. An exhaust treatment system for an engine, the system comprising:
   a particulate matter filter configured to filter particulate matter in exhaust produced by the engine;
   an exhaust outlet;
   a particulate matter sensor configured to be arranged in the exhaust outlet to measure particulate matter present in the engine exhaust with both a resistance sensor and a resonance sensor; and
   a sensor probe having a probe tip, the probe tip includes:
      the resistance sensor, a heater proximate to the resistance sensor to heat the resistance sensor, the resonance sensor, and an insulator insulating the resonance sensor from the heater.

10. The system of claim 9, wherein the resonance sensor is a piezoelectric sensor.

11. The system of claim 9, wherein the resonance sensor is an acoustic wave sensor.

12. The system of claim 9, wherein the insulator insulates the resonance sensor from the resistance sensor.

13. The system of claim 9, wherein the insulator is a heat shield insulating the resonance sensor from the resistance sensor.

14. The system of claim 9, wherein the insulator is a ceramic insulator insulating the resonance sensor from the resistance sensor.

15. The system of claim 9, wherein the heater is configured to heat the resistance sensor to regenerate the resistance sensor.

* * * * *